United States Patent [19]

Appleyard et al.

[11] Patent Number: 5,595,883

[45] Date of Patent: Jan. 21, 1997

[54] METHOD OF DIAGNOSING ALZHEIMER'S DISEASE BY MEASURING ACETYLCHOLINESTERASE ACTIVITY IN OCULAR FLUID

[75] Inventors: Margaret E. Appleyard, Egham; Brendan McDonald, Cowley, both of England

[73] Assignee: E. R. Squibb & Sons, Inc., Princeton, N.J.

[21] Appl. No.: 531,613

[22] Filed: Jun. 1, 1990

[51] Int. Cl.$^6$ ................ C12Q 1/46; C12Q 1/44
[52] U.S. Cl. ................ 435/20; 424/9.1; 435/19
[58] Field of Search ............ 435/19, 20; 424/9.1

[56] References Cited

PUBLICATIONS

Chipperfield, B. et al., "Plasma Cholinesterase Activities in Dementias, Depressions, and Schizophrenia," *Biological Abstracts* 85:62284, 1988.

Atack, J. R. et al., "Cerebrospinal Fluid Cholinesterases in Aging and in Dementia of the Alzheimher type," *Biological Abstracts* 85:105454, 1988.

Yamamoto, Y. et al., "Plasma and Serum G4 isoenzyme of Acetylcholinesterase in Patients with Alzheimer–type Dementia and Vascular Dementa," *Biological Abstracts*, 90:92062, 1990.

Mattio, T. G. et al (1984) "Effects of DFP on iridic metabolism and release of acetylcholine and on pupillary function in the rat," Neuropharmacology, 23, 1207–1214.

Hutchins, H. B. and Hollyfield, M. G. (1987) "Acetylcholinesterase in the human retina," Brain Res. 400, 300–311.

De Roeth, A. (1950) "Cholinesterase activity in ocular tissues and fluids," Arch. Ophthalmol. 43, 1004–1025.

Appleyard, M. E., et al (1987) Brain 110, 1309–1322.

*Primary Examiner*—David M. Naff
*Attorney, Agent, or Firm*—Burton Rodney

[57] ABSTRACT

A method is provided for diagnosing of senile dementia of the Alzheimer type (Alzheimer's disease) by measuring acetylcholinesterase (AChE) activity in ocular fluids and determining if such AChE activity is elevated over that found in ocular fluids of patients who do not have Alzheimer's disease. A level of AChE activity in the ocular fluid of a patient less than 30% higher than the level of AChE activity in the ocular fluids of a significant number of age-matched controls signifies the absence of Alzheimer's disease. A level of AChE activity in the ocular fluid of a patient at least about 35% higher than the level of AChE activity in the ocular fluids of a significant number of age-matched controls signifies the presence of Alzheimer's disease.

6 Claims, 2 Drawing Sheets

METHOD OF DIAGNOSING ALZHEIMER'S DISEASE BY MEASURING ACETYLCHOLINESTERASE ACTIVITY IN OCULAR FLUID

FIELD OF THE INVENTION

The present invention relates to a method of diagnosing for senile dementia of the Alzheimer type (SDAT or Alzheimer's disease) by measuring acetylcholinesterase (AChE) activity in the ocular fluids of a patient.

BACKGROUND OF THE INVENTION

It is known that appreciable levels of AChE are present in ocular tissues such as the amacrine cells of the retina (Hutchins, H. B. and Hollyfield, M. G. (1987) "Acetylcholinesterase in the human retina" Brain Res. 00, 300–311), and the nerve plexuses of the iris (Mattio, T. G. et al, (1984) "Effects of DFP on iridic metabolism and release of acetylcholine and on pupillary function in the rat" Neuropharmacology, 23, 1207–1214). It would therefore be expected that any secretion of AChE from such tissues would result in detectable levels of enzymatic activity within the fluids of the eye. Although there are some reports from the 1940s of cholinesterase activity in ocular fluids of various mammalian species (De Roeth, A., (1950) "Cholinesterase activity in ocular tissues and fluids," Arch. Ophthalmol. 43, 1004–1025) no attempt was made to distinguish between AChE and butyrylcholinesterase (BuChE) activities. Furthermore, these reports have not been confirmed by modern assay methods.

Patients with senile dementia of the Alzheimer-type (SDAT) frequently have defects in visual perception and find difficulties in performing visual tasks. Histological and electrophysiological studies indicate that these defects may be due to degenerative changes at all levels of the visual pathways, including loss of retinal ganglion cells and axonal degeneration of the optic nerve. The lower levels of acetylcholinesterase (AChE) observed in the post-mortem brains of patients with SDAT as a result of neuronal degeneration are reflected by lower levels of AChE in ventricular cerebrospinal fluid (CSF) obtained at post-mortem (Appleyard, M. E., et al (1987) Brain 110, 1309–1322).

Inasmuch as it is well established that AChE is present in ocular tissue including in the inner plexiform layer of human retina, if there are differences in the AChE content of fluids from patients with histologically diagnosed SDAT and normal aged-matched controls, these differences could be employed in diagnosing the presence or absence of SDAT.

DESCRIPTION OF THE INVENTION

In accordance with the present invention, a method is provided of diagnosing or detecting presence of SDAT also referred to as Alzheimer's disease, which method is based upon the difference in acetylcholinesterase (AChE) activity in the ocular fluids of patients with histologically diagnosed Alzheimer's disease and normal aged-matched controls.

The method of the present invention of diagnosing or detecting the presence of Alzheimer's diseases includes the steps of measuring the level of AChE activity in ocular fluids of a patient, and determining if such level of AChE activity is above the level of AChE activity found in ocular fluids in normal, preferably age-matched, controls. It has been found that patients with Alzheimer's disease will usually have a level of AChE activity in ocular fluids of at least about 30% greater than the average level of AChE activity found in ocular fluids of a significant number of normal age-matched controls.

Accordingly, where in carrying out the method of the present invention, it is determined that the level of AChE activity in ocular fluids of a patient is determined to be less than about 30% greater than the average level of AChE activity found in ocular fluids of normal age-matched controls, a negative diagnosis of Alzheimer's disease may be made.

Where in carrying out the method of the present invention, it is determined that the level of AChE activity in ocular fluids of a patient is determined to be more than about 35% greater than the average level of AChE activity found in ocular fluids of normal age-matched controls, a positive diagnosis of Alzheimer's disease may be made.

Where it is determined that the level of AChE activity in ocular fluids of a patient is determined to be more than about 30% greater but less than about 35% greater than the average level of AChE activity found in ocular fluids of normal age-matched controls, a diagnosis for Alzheimer's disease would be inconclusive.

The test employed for determining levels of AChE activity in both patients and controls are as described by Ellman, G. L., Courtney, D. K., Andres, V. and Featherstone, R. M. (1961) "A new and rapid colorimetric determination of acetylcholinesterase activity," Biochem. Pharmacol. 7, 161–177, and Chubb, I. W. and Smith A. D. (1975) "Isoenzymes of soluble and membrane-bound acetylcholinesterase in bovine splanchnic nerve and adrenal medulla," Proc. R. Soc. B 191, 245–261.

The method of the invention may be carried out while the patient is alive or at post-mortem.

The term "ocular fluid(s)" as employed herein refers to either or both the aqueous humor and the vitreous humor.

EXAMPLE 1

Figure 1:
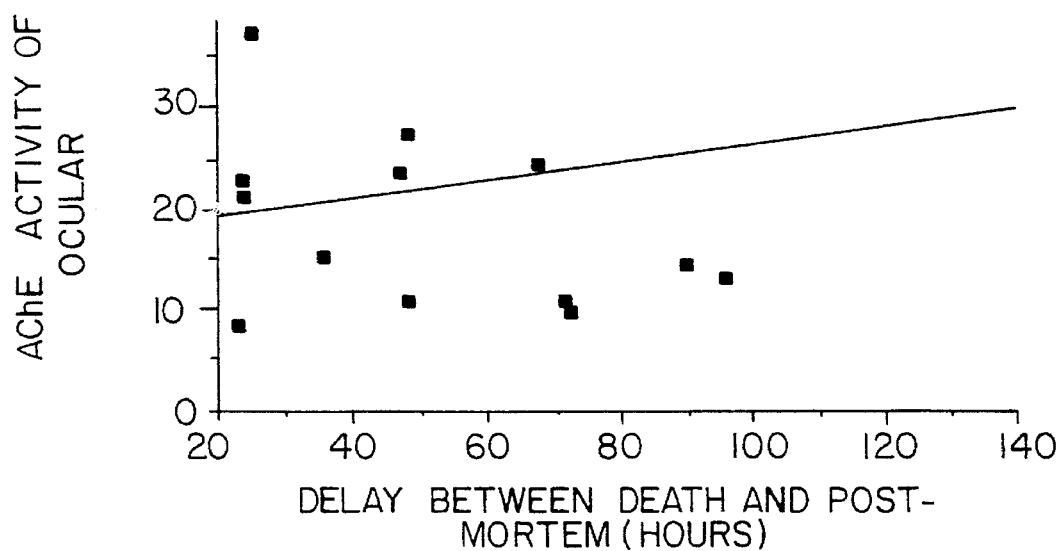
FIGS. 1 and 2 are graphs which show the relationship between AChE activity of ocular fluid obtained at post-mortem and the delay between death and post-mortem (FIG. 1) and the age of the patient at death (FIG. 2)

The following experiment was carried out to demonstrate the possible secretion of AChE from neuronal structures within the human eye. Human ocular fluids were examined for the presence of AChE and BuChE activities. In addition, the AChE forms present in ocular fluids were compared by polyacrylamide gel electrophoresis with that present in human cerebrospinal fluid (CSF) which is thought to derive, by secretion, from neuronal structures of the central nervous system.

Methods

Collection of Ocular Fluids a) at post mortem

Ocular fluids were collected at autopsy examination from individuals dying from non-neurological conditions and where a past history of eye disease was absent. The eyelids were retracted by hand and aqueous humor was collected from the anterior eye chamber by direct puncture through the cornea using a 25 G needle attached to a sterile 1 mL syringe followed by gentle aspiration of the contents. Similarly, the vitreous humor was collected from the anterior eye chamber by direct puncture through the sclera, posterior to the ciliary body, using a 27 G needle attached to a sterile 2 mL syringe. Any samples where there was discoloration of the fluid suggesting possible contamination by either iris or retina, were discarded. The normal cosmetic appearance of the eye was reconstituted by injecting a similar volume of saline back into the eye chambers.

The ocular fluids were transferred from the syringe to 1.5 mL microfuge tubes and centrifuged for 10 minutes at 12,000 g to sediment particulate matter. The supernatant was then gently aspirated off into another microfuge tube, labelled, snap frozen in liquid nitrogen and stored at −70° C.

b) during eye surgery

Aqueous humors were collected during eye surgery (for cataracts removal) from individuals with no history of other eye diseases or neurological disease. The skin of the eyelids was prepared for surgery with iodine solution, then dried. The lids were then held open with a speculum and an initial corneal groove made with a diamond knife. A 27 G sterile needle was then passed into the anterior chamber via the corneal groove and approximately 0.1–0.15 mls of aqueous humor removed into a 1 mL syringe. This was transferred straight into a sterile microfuge tube and frozen at −20° C. within 1 hour.

In six of the patients the surgical procedures were carried out under local anaesthesia (xylocaine) and samples were taken within 10 minutes of retro-bulbar injection. The remainder received a general anaesthetic, samples being taken 10–15 minutes after induction of anaesthesia. All patients received premedication consisting of phenylephrine and cyclopentolate.

Biochemical Analysis

Cholinesterase activities were measured by a microversion of the method of Ellman et al, (1961) supra, using microtitre plates. Acetylthiocholine was used as substrate at a concentration of 1.0 mM, which is optimal for AChE, but suboptimal for BuChE. The assay was performed in 0.05M Na/K phosphate buffer, pH 7.0 at 25° C., containing 3 mM 5,5'-dithio-bis-(2-nitrobenzoate), in a total volume of 100 µL. The rate of hydrolysis of acetylthiocholine was monitored by measurement of absorbances at 410 nm, using a Titertek multiscan microplate reader. A calibration curve was constructed using purified electric eel AChE (Sigma). AChE and BuChE activities were distinguished by use of the specific AChE inhibitor 1,5-bis-(-4-allyldimethylammoniumphenyl)pentan-3-one dibromide (BW 284c51) (1.5 µM).

Estimation of the protein content of the ocular fluids was performed by a micro version of the Biorad dye-binding assay (Bradford, M. (1976) Anal. Biochem. 72, 248).

Samples of ocular fluids and CSF were analysed by polyacrylamide gel electrophoresis. The gels were incubated with acetylthiocholine to reveal bands of cholinesterase activity (Chubb and Smith, 1975, supra), using BW 284c51 to distinguish between AChE and BuChE.

Results

Cholinesterase activity was detectable in all samples of ocular fluid examined, using acetylthiocholine as substrate. Most of this activity was inhibited by the specific AchE inhibitor BW 284c51 indicating that the majority of cholinesterase activity was attributable to AChE, whilst levels of non-specific cholinesterase activity were comparatively low. The AChE activities of total ocular fluid obtained at post-mortem were much higher than those detected in aqueous humor obtained during surgery from living patients (Table 1). When aqueous and vitreous humors were obtained separately at post-mortem, the AChE activity of the vitreous humor was higher than that of aqueous humor from the same eye (Table 1).

Figure 2:
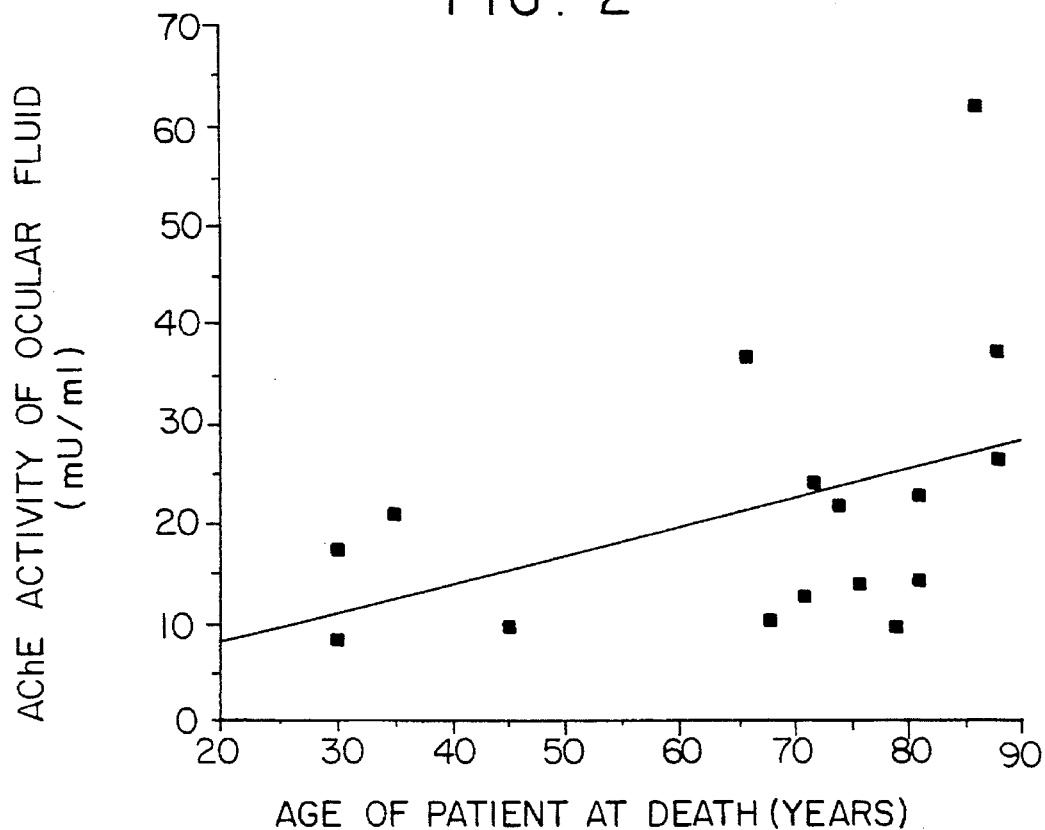

There was no significant correlation between AChE activity of the total ocular fluid obtained at post-mortem and the delay between death and post-mortem (FIG. 1). However, there was a significant correlation between AChE activity of total ocular fluid and the age of the patient at death, with a Spearman-Rank correlation coefficient of 0.542 (n=17) (FIG. 2).

Polyacrylamide gel electrophoresis of total ocular fluid revealed one band of AChE acitvity with a similar mobility to that of AChE in CSF obtained from the cisterna magna of the same patient.

Comparison of the cholinesterase activities of ocular fluid and cisternal CSF obtained at post-mortem indicates that ocular fluids contain slightly higher levels of AChE activity, but considerably lower levels of BuChE activity than cisternal CSF (Table 2). The specific activity of AChE in ocular fluid was markedly higher than that of cisternal CSF, due to the much lower levels of protein present (Table 2).

Discussion

These results show that AChE is present in human ocular fluids in appreciable levels whilst levels of BuChE are very low. The levels of AChE detectable in total ocular fluids obtained at post-mortem are comparable to those found in CSF also obtained at post-mortem from the same patient, although they are slightly higher.

The levels of AChE detectable in total ocular fluids obtained at post-mortem are markedly higher than those present in aqueous humor obtained from living patients during eye surgery. This could be explained if the majority of AChE activity observed in total ocular fluid at post-mortem is derived from the vitreous humor rather than the aqueous humor. The lower levels of AChE activity observed in the aqueous humor compared to the levels in vitreous humor in the few patients from whom the two fluids were collected separately would appear to support this explanation. The results of previous studies in the 1940s also suggest that most of the cholinesterase activity present in ocular fluids is confined to the vitreous humor (de Roeth 1950, supra). This is not surprising since it is the vitreous humor and not the aqueous humor which is in contact with the retina where the majority of AChE-containing cells of the eye are situated. It is likely that some mixing of the two pools of fluid would have occurred during the time between death and post-mortem, thus accounting for the higher levels of AChE found in aqueous humor obtained at post-mortem compared to the levels found in living patients.

An alternative explanation for the higher levels of AChE observed at post-mortem is that they are a post-mortem artefact due to the non-specific release of AChE from the tissues of the eye during the period between death and collection at post-mortem. However, if this were the case then the level of AChE activity present in the fluid samples should correlate with the time delay between death and post-mortem. As these two parameters were not correlated this explanation is unlikely.

The drug regimes of the patients could also contribute to these differences in AChE activity since various drugs have been shown to affect the secretion of AChE from the central nervous system into CSF (Greenfield, S. A. et al, (1979) "The effect of chlorpromazine on the concentration of acetylcholinesterase activity in the cerebrospinal fluid of rabbits" *Neuropharmacology,* 18, 127–132). Certainly all the surgical patients received the muscarinic antagonist cyclopentolate during premedication and such type of drug has been shown to decrease the secretion of AChE into CSF (Vogt, M. et al, 1984, "Factors influencing the cholinesterases of cerebrospinal fluid in the anaesthetised cat" *Neuroscience,* 12, 797–995). and from the hippocampus (Appleyard and Smith, 1987, "Spontaneous and carbachol-evoked in vivo secretion of acetylcholinesterase from the hippocampus of the rat," *Neurochem. Int.* 11, 397–406). It is therefore possible that this drug also decreases secretion of AChE from cholinergic tissues of the eye.

The AChE activity of total ocular fluid obtained at post-mortem was found to increase with the age of the patient such that the two were significantly correlated. Previous studies have found a similar effect of age on the AChE activity of CSF (Tune, L. et al, 1985, "Cerebrospinal fluid acetylcholinesterase activity in senile dementia of the Alzheimer type" *Ann. Neurol.* 17, 120–131; Appleyard et al, 1987, supra).

Polyacrylamide gel electrophoresis indicates that the AChE present in ocular fluid has a similar mobility to that of human CSF; indeed the two activities comigrate in a mixture of the two fluids. The form of AChE present in ocular fluids is therefore likely to be the same as that in CSF. Since the AChE activity in CSF is believed to result from secretion of AChE from the surrounding neuronal tissues it is also likely that the AChE found in ocular fluids is a result of secretion from the AChE-containing tissues of the eye.

In vitro studies have previously failed to demonstrate any secretion of AChE from the iris (De Sarno et al, 1987, "Release of acetylcholinesterase from the caudate nucleus of the rat," *J. Neurosci. Res.* 18, 578–590), which contains appreciable amounts of AChE in nerve plexuses. The results of the present study suggest that secretion of AChE from the tissues of the iris is negligible, at least in humans, since aqueous humor which is in close contact with the iris contains little AChE acitvity when collected during life.

TABLE 1

Cholinesterase activities of different types of human ocular fluid obtained either at post-mortem (PM) or at eye surgery.

| Ocular fluid | Total ChE acitivity | AChE activity | % AChE |
|---|---|---|---|
| PM poole fluids (n = 18) | 31.4 ± 3.8 | 23.9 ± 3.3 | 75.4 ± 2.9 |
| PM vitreous humor (n = 5) | 20.6 ± 2.0 | 14.7 ± 1.5 | 70.7 ± 1.9 |
| PM aqueous humor (n = 5) | 22.6 ± 1.2 | 11.4 ± 1.2 | 51.3 ± 5.2 |
| Surgical aqueous humor (n = 8) | 3.9 ± 0.3 | 2.6 ± 0.5 | 79.4 ± 7.2 |

TABLE 2

Comparison of cholinesterase activities of ocular fluid and cisternal CSF obtained at post-mortem from the same patients.

| Enzyme | total ocular fluid | cisternal CSF |
|---|---|---|
| AChE | 23.9 ± 3.3 | 21.0 ± 4.2 |
| BuChE | 13.8 ± 2.2 | 36.4 ± 13.9 |
| Protein | 0.84 ± 0.16 | 3.7 ± 0.8 |
| specific acitivity AChe | 37.5 ± 5.9 | 3.7 ± 0.9 |

XH3

Summary

Samples of ocular fluid obtained from normal individuals at autopsy and during eye surgery have been assayed for the presence of acetylcholinesterase. Measurable levels could be detected in all samples examined but levels of acetylcholinesterase in vitreous humor were consistently higher than those in aqueous humor, indicating a possible retinal origin. Polyacrylamide gel electrophoresis revealed that the acetylcholinesterase of ocular fluid had the same mobility of that of acetylcholinesterase from cerebrospinal fluid. It is probable that acetylcholinesterase is secreted from neuronal structures in the retina into the ocular fluid in an analogous manner to the secretion of acetylcholinesterase from brain neurones into cerebrospinal fluid.

EXAMPLE 2

The following working example describes the method of the invention carried out at post-mortem.

Samples of total ocular fluid (aqueous humor and vitreous humor) obtained at post-mortem were examined to see whether there were any differences in the AChE content of fluids from patients with histologically diagnosed SDAT and normal aged controls.

Samples of ocular fluid at post-mortem were collected and examined as described in Example 1.

AChE activity was detectable in all samples of ocular fluid examined, but when aqueous and vitreous humors were obtained separately the AChE activity of the vitreous humor was consistantly higher than that of aqueous humor from the same eye. The presence of AChE in ocular fluid is unlikely to be a post-mortem artefact since there was no correlation between AChE activity and post-mortem delay.

Figure 3:
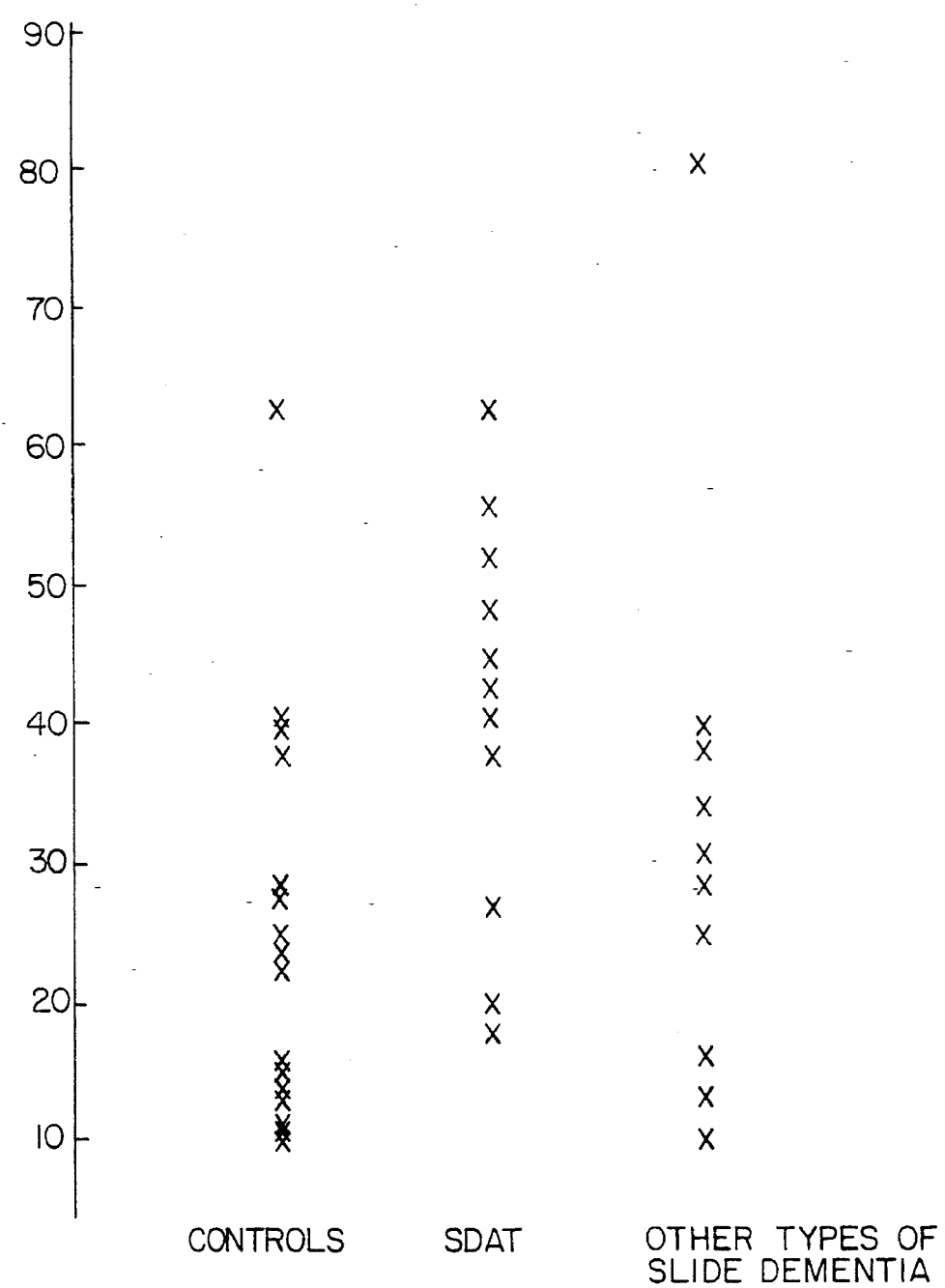
FIG. 3 is a graph showing AChE activity of ocular fluids from patients with different types of dementia.

The levels of AChE activity in total ocular fluid samples from patients with a clinical and histological diagnosis of SDAT were significantly higher than those observed in samples from normal age-matched controls (by an average of about 45%). (See Tables 3, FIG. 3 and Table 4).

It is concluded that AChE is normally secreted from the retina and appears in vitreous humor, in an analogous manner to its secretion from the brain into CSF. Such retinal secretion of AChE appears to be enhanced in patients with SDAT. This is in contrast to the situation in the brain where AChE-containing neurons degenerate and secretion appears to decrease.

TABLE 3

AChE activities of pooled ocular fluids obtained at post-mortem.

| Patients | AChE Activity | Comments |
| --- | --- | --- |
| Controls 1 | 27.5 | |
| | 37.5 | |
| | 22.9 | |
| | 14.8 | |
| | 11.1 | |
| | 10.8 | |
| | 15.5 | |
| | 23.9 | |
| | 38.2 | |
| | 40.5 | |
| | 24.8 | |
| | 13.5 | |
| | 62.5 | |
| | 10.2 | |
| Alzheimer's | 55.6 | |
| | 52.0 | mild Alzheimer's (AD) |
| | 62.4 | mild |
| | 42.2 | mild |
| | 27.1 | familial, severe AD changes |
| | 18.3 | moderate AD |
| | 20.1 | mild |
| | 44.5 | Down's, severe AD changes |
| | 44.8 | Down's, servere AD changes |
| Alzheimer's | 40.9 | mild |
| | 47.9 | familial, severe AD changes |
| | 37.9 | moderate AD |
| Other dementias | 80.5 | multi-infarct |
| | 40.0 | multi-infarct |
| | 29.0 | multi-infarct |
| | 31.2 | Pick's disease |
| | 25.0 | striatonigral degerneration |
| | 34.7 | Parkinson's/dementia |
| | 38.8 | schizophrenia/dementia1 |
| | 16.4 | memory disturbance |
| | 13.5 | hepatic enceph |
| | 10.7 | dialysis enceph |
| Parkinson's | 20.8 | |
| (no dementia) | 7.4 | |

TABLE 4

| Patients | Means ± SEM AChE Activity |
| --- | --- |
| Control (n = 14) | 25.3 ± 4.0 |
| Alzheimer's (n = 12) | 41.1 ± 3.9* |
| Other dementias (n = 10) | 32.0 ± 6.3 |

What is claimed is:

1. A method for detecting Alzheimer's disease, which comprises measuring the level of acetylcholinesterase activity in ocular fluids of a patient, and determining if such level of acetylcholinesterase (AChE) activity is above the average level of acetylcholinesterase activity found in ocular fluids in normal controls.

2. The method as defined in claim 1 wherein the measured level of acetylcholinesterase activity in said ocular fluids of said patient is compared to the average level of acetylcholinesterase activity found in ocular fluids in normal age-matched controls.

3. The method as defined in claim 1 wherein the measured levels of AChE activity found in ocular fluids of a patient is less than 30% higher than the level of AChE activity in ocular fluids of a significant number of age-matched controls, thereby signifying absence of Alzheimer's disease in said patient.

4. The method as defined in claim 1 wherein the measured levels of AChE activity found in ocular fluids of a patient is at least about 35% higher than the level of AChE activity in ocular fluids of a significant number of age-matched controls thereby signifying presence of Alzheimer's disease in said patient.

5. A method of diagnosing for Alzheimer's disease comprising the steps of determining the level of AChE activity in ocular fluids of a patient, comparing said level of AChE activity in ocular fluids of said patient with the level of AChE activity in ocular fluids of age-matched controls, determining if said level of AChE activity in ocular fluids of said patient is less than about 30% greater than the level of AChE activity in said age-matched controls, and if the difference in said levels of AChE activity is less than about 30%, making a diagnosis that said patient does not have Alzheimer's disease.

6. A method of diagnosing for Alzheimer's disease, which comprises determining the level of acetylcholinesterase (AChE) activity in the ocular fluids of a patient, comparing said level of AChE activity in the ocular fluids of said patient with the level of AChE activity in the ocular fluids of age-matched controls, determining if the difference in level of AChE activities in said ocular fluids is greater than 35% and, if the level of AChE in the ocular fluids of said patient is more than 35% greater than in age-matched controls, making a positive diagnosis of Alzheimer's disease.

* * * * *